US012582754B2

(12) United States Patent (10) Patent No.: US 12,582,754 B2
Nilsson (45) Date of Patent: Mar. 24, 2026

(54) KIT AND METHOD FOR REDUCTION OF COMPONENTS IN A BLOOD-RELATED MEDIUM

(71) Applicant: GLYCOPROBE AB, Lund (SE)

(72) Inventor: Kurt Nilsson, Trelleborg (SE)

(73) Assignee: GLYCOPROBE AB, Lund (SE)

( * ) Notice: Subject to any disclaimer, the term of this patent is extended or adjusted under 35 U.S.C. 154(b) by 537 days.

(21) Appl. No.: 17/923,383

(22) PCT Filed: May 6, 2021

(86) PCT No.: PCT/SE2021/050429
§ 371 (c)(1),
(2) Date: Nov. 4, 2022

(87) PCT Pub. No.: WO2021/225507
PCT Pub. Date: Nov. 11, 2021

(65) Prior Publication Data
US 2023/0355849 A1 Nov. 9, 2023

(30) Foreign Application Priority Data

May 7, 2020 (SE) .................................... 2000086-5
Jun. 24, 2020 (SE) .................................... 2000110-3

(51) Int. Cl.
*A61K 35/16* (2015.01)
*A61M 1/02* (2006.01)
(Continued)

(52) U.S. Cl.
CPC ........... *A61M 1/0218* (2014.02); *A61K 35/16* (2013.01); *A61M 1/0259* (2013.01);
(Continued)

(58) Field of Classification Search
CPC .............. A61M 1/0218; A61M 1/0259; A61M 1/3679; A61M 2202/0413;
(Continued)

(56) References Cited

U.S. PATENT DOCUMENTS 4,614,513 A 9/1986 Bensinger
2014/0284274 A1 9/2014 Nilsson
(Continued)

FOREIGN PATENT DOCUMENTS

CN 106668975 A 5/2017
EP 0 109 531 A1 5/1984
(Continued)

OTHER PUBLICATIONS

Supplementary European Search Report dated Apr. 2, 2024 for European Patent Application No. EP21 79 9756 (2 pages).
(Continued)

*Primary Examiner* — John Kim
(74) *Attorney, Agent, or Firm* — Smith, Gambrell & Russell, LLP

(57) ABSTRACT

A kit for reduction of blood components in a blood-related medium (12) is disclosed, wherein it comprises a gel bead container (1) containing gel beads (2) and provided with an outlet tube (3), a drip chamber (4) provided with an inlet tube (5) and an outlet tube (6), a collection container (10) provided with an inlet tube (11), and a medium container (13) adapted to contain a blood-related medium (12) and provided with an outlet tube (15), wherein the outlet tube (3) of the gel bead container (1) is connectable with the inlet tube (5) of the drip chamber (4) via a sterile connecting device, wherein the outlet tube (6) of the drip chamber is connectable with the inlet tube (11) of the collection container (10) via a sterile connecting device, and wherein the outlet tube (15) of the medium container (13) is connectable
(Continued)

to the inlet tube (5) of the drip chamber (4) via a sterile connecting device, as well as a method for reduction of blood components in a blood-related medium (12) by use of said kit.

20 Claims, 1 Drawing Sheet

(51) Int. Cl.

| | |
|---|---|
| *A61M 1/36* | (2006.01) |
| *A61P 31/14* | (2006.01) |
| *B01J 20/24* | (2006.01) |
| *B01J 20/26* | (2006.01) |
| *B01J 20/28* | (2006.01) |
| *B01J 20/32* | (2006.01) |
| *G01N 33/80* | (2006.01) |

(52) U.S. Cl.

CPC ........... *A61M 1/3679* (2013.01); *A61P 31/14* (2018.01); *B01J 20/24* (2013.01); *B01J 20/26* (2013.01); *B01J 20/28019* (2013.01); *B01J 20/28047* (2013.01); *B01J 20/2805* (2013.01); *B01J 20/3212* (2013.01); *B01J 20/3274* (2013.01); *B01J 20/3293* (2013.01); *G01N 33/80* (2013.01); *A61M 2202/0413* (2013.01); *A61M 2202/0415* (2013.01)

(58) Field of Classification Search

CPC  A61M 2202/0415; A61K 35/16; A61P 31/14; B01J 20/24; B01J 20/26; B01J 20/28019; B01J 20/28047; B01J 20/2805; B01J 20/3212; B01J 20/3274; B01J 20/3293; G01N 33/80

See application file for complete search history.

(56) References Cited

U.S. PATENT DOCUMENTS

| | | | |
|---|---|---|---|
| 2018/0065062 A1 | 3/2018 | Rae et al. | |
| 2023/0302429 A1* | 9/2023 | Nilsson | ..................... A61L 2/06 |

FOREIGN PATENT DOCUMENTS

| | | |
|---|---|---|
| EP | 1 611 908 A2 | 1/1997 |
| JP | S58-165859 A | 9/1983 |
| WO | 2013/062479 A1 | 5/2013 |

OTHER PUBLICATIONS

International Search Report dated Jun. 2, 2021 for International Patent Application No. PCT/SE2021/050429 (5 pages).

Written Opinion of the International Searching Authority dated Jun. 2, 2021 for International Patent Application No. PCT/SE2021/050429 (8 pages).

International Preliminary Report on Patentablilty dated Jun. 9, 2022 for International Patent Application No. PCT/SE2021/050429 (7 pages).

Rydberg, L., et al. In vitro assessment of a new ABO immunosorbent with synthetic carbohydrates attached to sepharose. Transpl Int. 2005. vol. 17, pp. 666-672.

* cited by examiner

KIT AND METHOD FOR REDUCTION OF COMPONENTS IN A BLOOD-RELATED MEDIUM

TECHNICAL FIELD

The present invention refers to a kit and a method for reduction of components in a blood-related medium.

BACKGROUND ART

The problems with presently used devices and methods for the reduction of undesired components from blood and other biological fluids are that there is a constant need of blood related products, such as whole blood, blood plasma (e.g. as replacements in surgical and apheresis procedures and in trauma situations), platelets (thrombocyte preparations), blood serum and immunoglobulins. Shortage situations arise of whole blood, blood plasma and platelets. Immunoglobulin preparations can lead to severe side reactions due to blood group incompatible antibodies. There are blood plasma products on the market with reduced content of blood group specific antibodies that in principle can be produced by pooling different plasma with low content (titer) of blood group specific antibodies or mixing plasma of different blood groups (e.g. A-plasma with AB-plasma) leading to immune complex formation between soluble blood group antigens in the AB-plasma with blood group specific antibodies. The formed immune complexes may however lead to side reactions. Blood typing is essential in transfusion and interfering antibodies can lead to wrong results. Thus, it has since long been a need of a method for reducing or eliminating these problems.

SUMMARY OF THE INVENTION

An object of the present invention is to provide an improved kit and an improved method for reduction of components in a blood-related medium by which the above-mentioned problems are solved. This object is achieved with a kit as described below. The object is also obtained with a method as described below involving the use of said kit. Particular and preferred embodiments are also disclosed In one aspect the present invention refers to a kit for reduction of blood components in a blood-related medium 12, wherein it comprises:

a gel bead container 1 containing gel beads 2 and provided with an outlet tube 3, a drip chamber 4 provided with an inlet tube 5 and an outlet tube 6, a collection container 10 provided with an inlet tube 11, and a medium container 13 adapted to contain a blood-related medium 12 and provided with an outlet tube 15, wherein the outlet tube 3 of the gel bead container 1 is connectable with the inlet tube 5 of the drip chamber 4 via a sterile connecting device, wherein the outlet tube 6 of the drip chamber is connectable with the inlet tube 11 of the collection container 10 via a sterile connecting device, and wherein the outlet tube 15 of the medium container 13 is connectable with the inlet tube 5 of the drip chamber 4 via a sterile connecting device.

In one embodiment of the inventive kit the drip chamber 4 is provided in the bottom thereof with a porous net 14 having a porosity which does not allow passage of the gel beads 2, and the inlet tube 5 of the drip chamber 4 is provided with a clamp 7.

In one embodiment of the inventive kit the outlet tube 6 of the drip chamber 4 is provided with a clamp 8, and with a roller clamp 9.

In one embodiment of the inventive kit the gel bead container 1, the collection container 10, and the medium container 13 are plastic bags.

In one embodiment of the inventive kit each tube is made of plastic and has the same inner diameter.

In one embodiment of the inventive kit the gel bead container 1 is a sterilized plastic bag containing a suspension of gel beads 2 in a liquid buffer.

In one embodiment of the inventive kit the drip chamber 4 is present in an outer plastic bag and is sterilized.

In one embodiment of the inventive kit the medium container 13 contains the blood-related medium 12, preferably human whole blood, blood plasma, or thrombocytes, most preferably human blood plasma.

In one embodiment of the inventive kit the gel beads 2 contain at least one covalently bound antigen or antigen derivative having the ability to bind at least one plasma component.

In one embodiment of the inventive kit the gel beads 2 contain at least one covalently bound antigen or antigen derivative which selectively bind an antigen specific protein or antibody.

In one embodiment of the inventive kit the antigen or antigen derivative contains a protein, a peptide, a carbohydrate, or a carbohydrate derivative.

In one embodiment of the inventive kit the gel beads 2 contain cross-linked agarose or a plastic, preferably polyhydroxymethacrylate or polyhydroxyethylacrylate.

In one embodiment of the inventive kit the carbohydrate derivative contains at least one blood group determinant, preferably a blood group A determinant, and/or a blood group B determinant.

In one embodiment of the inventive kit the carbohydrate derivative contains at least one of a disaccharide, tri-saccharide, tetra-saccharide and/or a higher oligosaccharide.

In another aspect the present invention refers to a method for the reduction of blood components in a blood-related medium 12 by use of the kit according to the present invention, wherein it comprises the steps of:

a) connecting the outlet tube 3 of the gel bead container 1 containing a suspension of gel beads 2 with the inlet tube 5 of the drip chamber 4, wherein the clamp 7 of the inlet tube 5 of the drip chamber 4 is closed, b) connecting the outlet tube 6 of the drip chamber 4 with the inlet tube 11 of the collection container 10, c) agitating the content of the gel bead container 1 containing gel beads 2 to obtain a suspension of gel beads 2, d) opening the clamp 7 of the inlet tube 5 of the drip chamber 4, e) transfer of the suspension of gel beads 2 to the drip chamber 4, wherein the clamp 8 and the roller clamp 9 of the outlet tube 6 of the drip chamber 4 are closed, f) disconnecting the outlet tube 3 of the gel bead container 1 from the inlet tube 5 of the drip chamber 4, g) connecting the outlet tube 15 of the medium container 13 containing the blood-related medium 12 with the inlet tube 5 of the drip chamber 4, h) opening the clamp 8 of the outlet tube 6 of the drip chamber 4 allowing transfer of the blood-related medium 12 from the medium container 13 to the drip chamber 4 and gradually opening the roller clamp 9 of the outlet tube 6 of the drip chamber 4 until a predetermined flow rate of the blood-related medium 12 is obtained, i) collecting the blood-related medium 12, which has passed the gel beads 2 in the drip chamber 4, in the collection container 10, wherein the gel beads 2 are prevented from reaching the collection container 10 due to the presence of the porous net 14 provided in the bottom of the drip chamber 4, and j) stopping the procedure when the blood-related medium 12 has passed from the medium container 13 to the collection chamber 10 via the drip chamber 4, or, alternatively, closing at least one of the clamp 7 and the clamp 8, replacing the medium container 13 with a new medium container 13 containing a new blood-related medium 12, and repeating steps h)-j).

In one embodiment of the inventive method the flow rate of the blood-related medium 12 is measured by counting the number of droplets dripping into the drip chamber 4 for a given time period.

In one embodiment of the inventive method the gel beads 2 present in the drip chamber 4 is washed with neutral buffer, followed by washing with acidic glycine buffer, with a view to eluting the component from the blood-related medium 12 bound to the gel beads 2, and collecting the eluted component(s).

In one embodiment of the inventive method the blood-related medium 12 is human whole blood, blood plasma, blood serum or thrombocytes, preferably human blood plasma.

In one embodiment of the inventive method the suspension of gel beads 2 in the gel bead container 1 instead is transferred to the medium container 13, wherein the suspension of gel beads 2 is mixed with the blood-related medium 12 therein, and wherein the mix of gel beads 2 and blood-related medium 12 is transferred to the drip chamber 4.

DETAILED DESCRIPTION OF THE INVENTION

Figure 1:
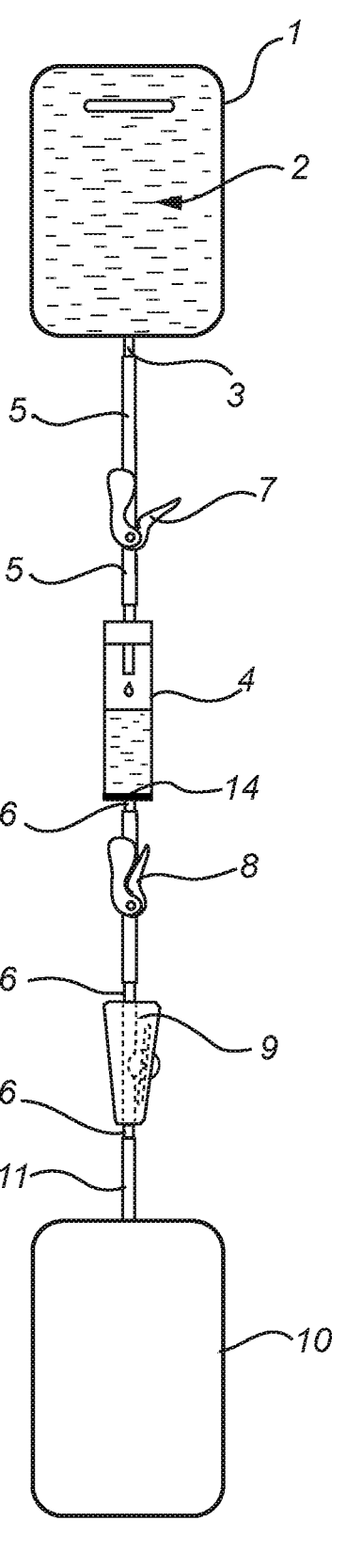
FIG. 1 shows a view of some of the kit parts connected with each other, more precisely the drip chamber 4 connected with both the outlet tube 3 of the gel bead container 1 via the inlet tube 5 and also with the inlet tube 11 of the collection container 10 via the outlet tube 6 of the drip chamber 4.

First, some expressions present in the application text will be defined.

The expression "blood-related medium 12" used throughout the application text is intended to mean a medium in the form of a biological fluid or liquid comprising components which are of interest to eliminate from said medium. Examples of the blood-related medium 12 are whole blood, blood plasma, blood serum or a solution of thrombocytes, in other words a solution containing one or more blood components. Said blood-related medium 12 may have a human or non-human origin, preferably a human origin. The expression "blood-related medium 12" is in the present context also intended to mean a blood-related medium 12 from which the components initially present therein have been reduced or eliminated, such as the medium collected in the collection container 10 in the method according to the present invention.

The expression "sterile connecting device" (not shown in the Figs.) used throughout the application text can be any device within the technical area which provides a sterile connection between two components. Examples of such devices are TSCD-II® (Terumo) or CompoDock® (Fresenius).

The advantages achievable with the present invention compared to the prior art are that the handling of the product is straightforward for the user, gravitation alone is used for creating a flow of blood related medium through the chamber, the flow rate is easily controlled, the sterile connection between the different parts is straightforward, and thereby the risk of contamination of the treated blood related medium with bacteria, viruses or particles is minimal. Moreover, no or a minimum of foreign components are added to the blood-related medium 12 that is treated during the inventive method. Said method has been found to be effective in the specific removal of the component desired to be removed without any significant influence on other components, e.g. in blood plasma and thrombocyte preparations or immunoglobulins. Thus, there is minimal or non-significant influence on e.g. total immunoglobulins due to the antigen specific binding of the component desired to be removed.

In both of the priority applications the kit and method features were denoted in the way as disclosed below in italics:

The method involves the use of the components 1, 2, 3 and 4 below:

1. A plastic bag containing g) a gel suspension containing gel beads in liquid buffer and b) a plastic tube connected to the plastic bag
2. An empty drip chamber containing c) a tube leading to the drip chamber, where the tube is closed with d) a clamp, e) a tube below the drip chamber, where the tube contains f) a clamp, g) a roller clamp and h) a porous net of a porosity which does allow passage of plasma with its components but which does not allow passage of gel beads
3. An empty plasma collection bag provided with i) a tube
4. A bag containing human blood plasma provided with j) a tube In the present application the denotations of these features have been amended to have the following correspondence to the language being shown in italics above and present in the priority applications.

The gel bead container 1 corresponds to component 1. The gel beads 2 corresponds to a) the gel suspension containing gel beads. The outlet tube 3 correspond to the plastic tube b). The drip chamber 4 corresponds to component 2. The inlet tube 5 corresponds to the tube c). The outlet tube 6 corresponds to the tube e). The clamp 7 corresponds to the clamp d). The clamp 8 corresponds to the clamp f). The roller clamp 9 corresponds to the roller clamp g). The collection container 10 corresponds to component 3. The inlet tube 11 corresponds to the tube i). The medium container 13 corresponds to component 4. The outlet tube 15 correspond to the tube j).

In the priority applications the following text in italics was also present.

The method is further characterized by the following steps:

i) The plastic tubes b and c are connected to each other using a sterile connecting device ii) The plastic tubes e and i are connected to each other using a sterile connecting device iii) The gel suspension a is agitated in order to disperse the gel suspension iv) Clamp d is opened and the gel suspension a is transferred to the drip chamber while clamps f and g are closed v) The tube of component 1 is disconnected from tube c of component 2 and the plastic tubes c and j are connected to each other using a sterile connecting device vi) The clamp f is opened and the roller clamp g is gradually opened until the desired flow rate of blood plasma is achieved vii) The flow rate of plasma is measured by counting the number of droplets dripping into the drip chamber for a given time period viii) The plasma passes the gel beads and is collected in component 3 ix) When all plasma has passed from component 4 to component 3 the procedure can be stopped or x) The procedure can optionally be repeated by closing one of the clamps d or f sealing tube c to the tube of a new plasma containing bag (component 4) and repeating steps vi-ix.

xi) Optionally the gel beads in the drip chamber can be washed with neutral buffer, followed by washing with acidic glycine buffer to elute plasma component bound to the gel beads and collecting the eluted plasma component.

In the present application the step features listed in connection with the method of the present invention correspond to the steps i)-xi) shown above in italics and disclosed in the priority applications.

Figure 2:
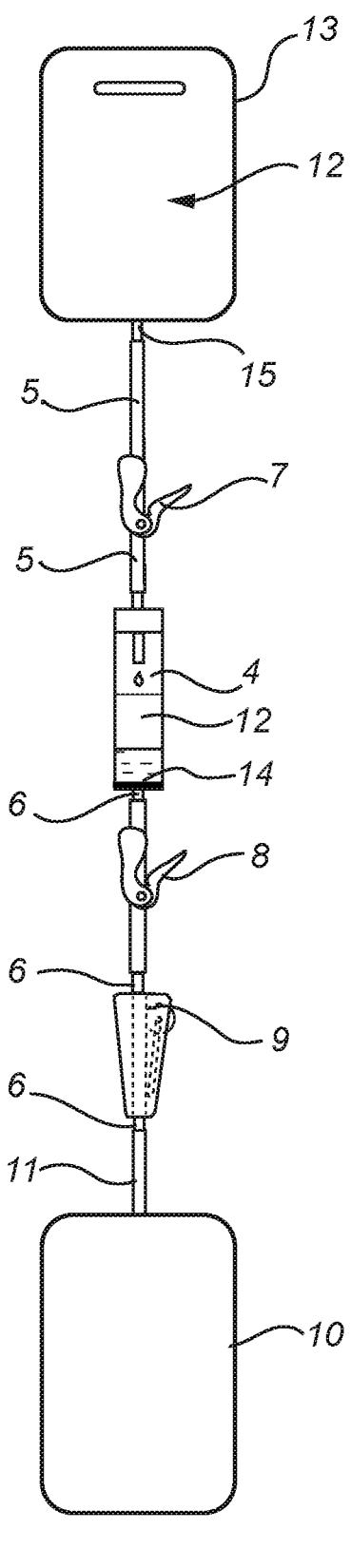
FIG. 2 shows another view of some of the kit parts connected to each other, more precisely the drip chamber 4 connected with the outlet tube 15 of the medium container 13 via the inlet tube 5 and also with the inlet tube 11 of the collection container 10 via the outlet tube 6 of the drip chamber 4.

The present invention will now be disclosed more in detail with reference to FIG. 1 and FIG. 2, which show two versions of connected kit parts.

Referring to FIG. 1, a gel bead container 1 is initially provided. The gel bead container 1 may be a bag provided with a tubing, e.g. a hemo-compatible plastic bag with a hemo-compatible tubing used for the filling of the suspension of gel beads 2 therein. In one embodiment a bottle with a tubing is used instead of a bag, but a bag is more preferred. After such a filling step the tubing is closed nearby the outlet with a view to preventing the suspension of gel beads 2 to exit the gel bead container 1. The filled gel bead container 1 is then placed in an enclosing outer bag, e.g. a plastic bag, which then is closed. This product is then end-sterilized with steam, e.g. at a temperature of 121° C. The inner volume of the gel bead container 1 depends on the specific application thereof, but an inner volume in the range of 10-60 mL is normally used. In FIG. 1. the above-mentioned outer enclosing bag has been removed and is therefore not shown.

The gel bead container 1 is provided with an outlet tube 3 for the exit of the content from the gel bead container 1, which is adapted to house the suspension of gel beads 2 in a liquid buffer. The volume of the gel beads 2 (the settled volume) when present therein is typically from 2 mL to 20 mL. The suspension of gel beads 2 contains a ratio of gel beads 2 to total volume of preferably from 30 to 45%. Further, the liquid buffer in which the gel beads 2 are suspended may contain citrate as an anticoagulant, e.g. in a CPD-containing buffer (citrate/phosphate/dextrose buffer).

As mentioned above, the gel bead container 1 is in one embodiment a plastic bag containing gel beads 2, which have been sterilized by use of steam autoclaving after having been placed in said plastic bag. The gel beads 2 are porous and the pores thereof allows entrance of proteins. Preferably, the pores allow entrance of proteins up to a size of 1 million Daltons, allowing IgG and IgM antibodies to enter the pores inside the gel beads 2. As an example, gel beads 2 made from cross-linked agarose can be mentioned to which at least one antigen has been covalently bound. The kit and the method used according to the present invention can also involve gel beads 2 made of plastics, such as polyhydroxymethacrylate or polyhydroxyethylacrylate.

The gel beads 2 are preferably spherical and have an average diameter of 40 to 200 μm, preferably 60-120 μm when the blood related medium is blood plasma or a solution containing immunoglobulins. For treatment of whole blood the larger size range is preferred. The diameter of the gel beads is higher than the porosity of the porous net 14 located in the bottom of the drip chamber 4. Typically, the porous net 14 has a porosity of 20 to 35 μm, preferably in the range 25-30 μm.

Further, the gel beads 2 contain one or more covalently bound antigens or antigen derivatives, which selectively can bind one or more blood components, such as antibodies or other blood proteins. Examples of antigens or antigen derivatives are those containing a peptide, protein, carbohydrate, or carbohydrate derivative. The quantity of the antigens or antigen derivatives is preferably from 1 mg per mL gel bead up to 10 mg per mL gel bead. Examples of carbohydrate antigens are disaccharides, tri-saccharides, tetra-saccharides or higher oligosaccharides with selectivity for blood group specific antibodies.

There are several known antibody or protein binding carbohydrate molecules and antibody binding antigens, such as different peptide or carbohydrate antigens, which specifically binds to antibodies. These can be used as antigens or antigen derivatives in the method according to the invention. Blood group determinants H, A, B and other blood group antigens are examples of such carbohydrates. One or more different carbohydrate antigens can be used in each application of the invention. Also, one or more of the different subtypes of the same type of blood group antigen can be used, e.g. blood group A or B antigens of e.g. subtypes 1, 2, 3 or 4.

Further, several different antigens or antigen derivatives may be present on each gel bead 2. Alternatively, a mixture of gel beads 2 having a certain antigen or antigen derivative bound thereto and of gel beads 2 having a different certain antigen or antigen derivative bound thereto may be present at the same time in the gel bead container 1 from the start with a view to reducing the amount of different components in the blood-related medium 12 at the same time.

Other examples of carbohydrate containing antigens are sialylated antigens, Lewis antigens, gangliosides, lectin- or galectin binding carbohydrates or carbohydrate derivatives, as well as Lewis-, P- and Ge-carbohydrate antigens and rare blood group antigens. Preferably, a glycoside derivative, i.e. containing an aglycon, of the carbohydrate antigen is used for covalent binding to the gel beads. The aglycon of the carbohydrate derivative is used for covalent binding to the gel beads 2 and can be an aliphatic and or aromatic compound containing e.g. an amino group, e.g. forming an amide linkage with a carboxyl group on the gel bead using e.g. an NHS-group on the carboxyl group during the coupling reaction.

Examples of peptide antigens or protein antigens are peptides, antibodies or proteins with the ability to selectively bind antibodies or other proteins in human plasma and whole blood.

In a subsequent step of the inventive method the outlet tube 3 of the gel bead container 1 is connected with the inlet tube 5 of the drip chamber 4, wherein the clamp 7 of the inlet tube 5 of the drip chamber 4 is closed.

The drip chamber 4 may be any one conventionally used in this technical field, but is in one embodiment made of hemo-compatible plastic materials that can be used with EtO sterilisation, such as ABS and phthalate free PVC. It is also provided with a porous filter 14 (e.g. with a pore size of 25 μm and made from e.g. polyamide) at the bottom of the drip chamber 4. The inner volume of the drip chamber 4 is typically from 5 mL to 60 mL. The drip chamber 4 can have different sizes depending on the desired volume of the suspension of gel beads 2, but in one embodiment the height of the drip chamber 4 is within the range of 70 to 100 mm and the width within the range of 10 to 20 mm. The length and diameter of the inlet tube 5 and the outlet tube 6 that are mounted to the drip chamber 4 is chosen to allow for sterile connection, by use of a standard connecting device as mentioned above, to a similar tube of the gel bead container 1, the medium container 13, and the collection container 10. In one embodiment the length of the inlet tube 5 is in the range of 150 to 250 mm, and the outlet tube 6 is preferably in the range of 400 to 500 mm.

The connection between the gel bead container 1 and the drip chamber 4 is made between the outlet tube 3 of the gel bead container 1 and the inlet tube 5 of the drip chamber 4, and the connection is made above the clamp 7 on the inlet tube 5 of the drip chamber 4. The drip chamber 4 is initially empty during the inventive method. In one embodiment the drip chamber 4 has been sterilized before use with ethylene oxide after having been placed in a sealed plastic bag. Thereafter the outlet tube 6 of the drip chamber 4 is connected with the inlet tube 11 of the collection chamber 10 by using a sterile connecting device. The latter connection step may alternatively be performed before the gel bead container 1 and the drip chamber 4 are connected. The collection chamber 10 is initially empty during the inventive method and is used for collecting the blood-related medium 12 that has passed the drip chamber 4.

Then the gel beads 2 in the gel bead container 1 is agitated, e.g. by gently pressing, in order to suspend the gel beads 2 in the buffer therein. Thereafter, the clamp 7 of the inlet tube 5 of the drip chamber 4 is opened, and the suspension of gel beads 2 is transferred to the drip chamber 4, while the clamp 8 and the roller clamp 9, arranged downstream of the clamp 8, of the outlet tube 6 of the drip chamber 4 are closed. The flow of the suspension of gel beads 2 down to the drip chamber 4 takes place by utilizing just the gravity, i.e. no pumps or other devices are needed. This facilitates the use of the inventive method for the practitioner, e.g. at blood banks.

FIG. 1 shows some of the kit parts connected to each other in a vertical arrangement, the gel bead container 1 being the uppermost kit part. More precisely, FIG. 1 shows the drip chamber 4 connected with both the gel bead container 1 and with the collection container 10 during a step corresponding to the end of the step of the transfer of the suspension of gel beads 2 from the gel bead container 1 to the drip chamber 4. Here the clamp 7, the clamp 8, and the roller clamp 9 are all closed. In the arrangement shown in FIG. 1 the gel bead chamber 1 may e.g. contain a suspension of a mixture of gel beads 2 containing blood group A determinant(s) covalently bound thereto and blood group B determinant(s) covalently bound thereto.

When the suspension of gel beads 2 has been emptied from the gel bead container 1, totally or to an intended extent, and has been transferred to the drip chamber 4, the clamp 7 is closed, and the outlet tube 3 of the gel bead container 1 is disconnected from the inlet tube 5 of the drip chamber 4. The outlet tube 15 of the medium container 13 is thereafter connected with the inlet tube 5 of the drip chamber 4 by use of a sterile connecting device, as defined above. The medium container 13 contains the blood-related medium 12, preferably human blood plasma, whole blood, or a thrombocyte preparation, most preferably blood plasma.

FIG. 2 shows some of the kit parts connected to each other in a vertical arrangement, the medium container 13 being the uppermost kit part. More precisely, FIG. 2 shows the drip chamber 4 connected with both the medium container 13 and with the collection container 10 during a step corresponding to the start of the passage of blood-related medium 12 from the medium container 13 through the drip chamber 4 and down to the collection chamber 10. Here the clamp 7, the clamp 8, and the roller clamp 9 are all opened.

Then the clamp 7 of the inlet tube 5 and the clamp 8 of the outlet tube 6 of the drip chamber 4 are opened, and the roller clamp 9 is gradually opened until a predetermined flow rate of the blood-related medium 12 entering the drip chamber 4 is obtained. The flow rate is measured by counting the number of droplets dripping into the drip chamber 4 for a given time period. The flow rate in the case of plasma as the blood-related medium is normally between 2 and 5 mL per minute, corresponding to between 40 and 100 droplets per minute. The porous net 14, having a porosity of 20-35 μm and located in the bottom of the drip chamber 4, prevents the gel beads 2 from entering the collection chamber 10.

Upon passage of the blood-related medium 12 from the medium container 13 through the gel beads 2 in the drip chamber 4 at least one blood component will selectively bind to the antigen(s) or antigen derivative(s) which is/are covalently bound to the gel beads 2. Thus, the content of the blood component in the blood-related medium 12 will be reduced or eliminated after passage through the gel beads 2.

The level of the blood-related medium 12 has to be kept below the lower end of the inlet tube 5 for the blood-related medium 12 in the drip chamber 4 to allow for the calculation of the flow rate by counting the number of droplets per minute that enters the drip chamber 4, i.e. there must be an air space above the surface of the blood-related medium 12 therein making it possible for drops to fall down on said surface. The level of the blood-related medium 12 in the drip chamber 4 should also be kept well above the level of the gel beads 2 therein in order not to disturb the bed of gel beads 2.

Optionally, the gel beads 2 in the drip chamber 4 can be washed with a neutral buffer, followed by washing with acidic glycine buffer to elute component(s) in the blood-related medium 12 which have been bound to the gel beads 2 and by separately collecting eluted plasma component that may be of interest to isolate.

When all or a desired volume of the blood-related medium 12 has passed from the medium container 13 to the collection chamber 10, the separation procedure is stopped, and the blood-related medium 12, now purified from undesired components, may be used for its intended purpose.

In an alternative embodiment the separation procedure may be continued by first closing the clamp 7, the clamp 8, and the roller clamp 9, replacing the medium container 13 with a new medium container 13 containing a new blood-related medium 12, and repeating method steps h)-i) above. The inlet tube 5 of the drip chamber 4 is also here connected by use of a sterilizing device with the outlet tube 15 of the new medium container 13 containing the new blood-related medium 12.

The dimensions of all of the above-mentioned tubes used in the kit and the method according to the present invention are of a diameter that allows for sterile connection, as described above, using a standard sterile connecting device known from the state of the art of sterile connection of tubes or lines. In one embodiment all the above-mentioned tubes are made of plastic and have the same or similar outer and inner diameter. In a preferred embodiment the tubes and plastics used in the gel bead container 2, the drip chamber 4, and the collection container 10 are all hemo- and bio-compatible to minimize the influence on blood components.

In a modified alternative use of the inventive method the suspension of gel beads 2 of the gel bead container 1 is first transferred to the medium container 13, which contains the blood-related medium 12, e.g. blood plasma, whole blood, or thrombocytes. This is followed by of mixing the suspension of gel beads 2 with e.g. the plasma, whole blood, or thrombocytes in the medium container 13. This is achieved e.g. by gentle rotation or end-over-end mixing of the gel beads 2 with the content in the medium container 13, preferably between 30 to 60 minutes and preferably at ambient temperature. The medium container 13 is thereafter connected with the drip chamber 4, and said mixture in the medium container 13 is transferred to the drip chamber 4 and then to the collection container 10, as illustrated in FIG. 2. In one embodiment, the passage of e.g. whole blood or thrombocytes through the drip chamber 4 can be performed as in FIG. 2, but by arranging the drip chamber 4 in a horizontal position instead of a vertical position to facilitate passage of whole blood through the drip chamber 4. By following the subsequent procedural steps disclosed above, the gel beads 2 are then separated from the plasma, whole blood, or thrombocytes.

The drip chamber 4, the tubes thereof, which can be made from a hemo-compatible plastic, e.g. PVC (+ DINCH), and clamps thereof may be stored before use in a closed and sterilized outer protective plastic bag, and may also be packed and delivered in a protective packaging e.g. paperboard. As mentioned above, the gel bead bag located within an outer protective bag is also sterilized and packed in a paperboard adapted to the product and the number of units. When to be used, the paperboards with the bag with the gel bead container 2 and the bag with the drip chamber 4, including all tubes and clamps, are opened, and the components therein are connected as disclosed above.

Examples

In an example of the method according to the present invention the method steps a)-j) were followed. The suspension of gel beads 2 used in the gel bead container 1 and transferred to the drip chamber 4 was a mixture of gel beads 2 containing at least one blood group A determinant covalently bound to gel beads 2 (2 mL) and at least one blood group B determinant covalently bound to gel beads 2 (2 mL). Donor plasma of blood group O (250 mL) was passed through the system, as shown in FIG. 2. In this case antibodies specific for blood group A antigen and blood group B antigen were bound to the gel, and these antibodies were reduced selectively with minimal influence on antibodies of other specificities and on other blood proteins or blood components. Thus, there was a minimal influence on coagulation times, coagulation factors, such as Factor VIII, complement factors and other proteins and blood components. The reduction of blood group A and blood group B specific antibodies (anti-A and anti-B antibodies, respectively) was measured by standard titration against red blood cells (of blood group A and blood group B, respectively). When using a blood plasma with a titer of e.g. 1:256, the titer was reduced (as measured in a sample taken from the collection container 10) to 1:8 or lower after having used the kit and the method according to the present invention.

The experiment was repeated with several blood group O donor plasmas from different blood donors having initial titers of from 1:32 up to high titers, (e.g. a titer of 1:1024) and similar results as above were obtained. It was found that up to 700 mL of plasma, i.e. approximately 3 different standard donor plasma bags, could be treated in sequence with similar results using the same gel beads 2 (a volume of 2 mL of blood group A-containing gel beads and 2 mL of blood group B-containing gel beads) and with the gel beads 2 being in the same drip chamber 4.

It is known that donor blood plasma (e.g. of blood group O) can be given to a recipient who has another and incompatible blood group, e.g. blood group A, B, or AB (the plasma is blood group incompatible due to that it contains blood group A- and B-specific antibodies in the plasma reacting), can be given to the recipient provided that the level of blood group A/B-specific antibodies is sufficiently low, (e.g. 1:16 or lower—also depending on the volume given), and therefore the treated plasma obtained by using the method and kit according to invention can be used as 'universal plasma'. Blood group A plasma can also be treated using the method and kit according to the present invention, wherein gel beads 2 with covalently bound blood group B antigen is used to remove anti-B antibodies in A plasma.

The method disclosed above was also used to treat so called convalescent plasma, i.e. plasma obtained from patients that had undergone an infection and who had developed antibodies towards a virus, e.g. an infection caused by the covid-19 virus. The treatment of the convalescent plasma with the method according to the present invention efficiently reduced the blood group specific antibody level, but did not affect the covid-19 specific antibody level to any significant degree. The resulting plasma was given successfully to seriously diseased covid-19 patients. The method and kit have also been shown not to influence convalescent plasma antibodies that are specific towards other viruses.

It was also found that anti-A and anti-B antibody reduced plasma could be remixed with blood group O red blood cells, resulting in whole blood of blood group O, but with a highly reduced content of blood group A and B specific antibodies which potentially could be given in an emergency situation, irrespective of the blood group of the recipient (universal whole blood).

In addition, it has been shown that thrombocyte preparations of blood group O could be treated with the inventive method, which resulted in thrombocyte preparations with significantly reduced levels of blood group A and B specific antibodies. This facilitates a potentially more efficient method for preparation of 'universal' thrombocyte preparations, i.e. thrombocytes that can be given irrespective of the blood group of the recipient.

In a further application e.g. blood group A and B specific antibodies may disturb determination of rare blood groups, and the method according to the present invention can therefore be of use by removing the disturbing antibodies in a plasma sample from the patient, thereby facilitating a better blood typing of the patient/plasma in these situations.

The method according to the present invention has also been shown to be effective in removal of undesired antibodies when applied for treatment of blood serum. Blood serum has a number of different applications, and problems can arise when the serum contains incompatible antibodies.

The invention claimed is:

1. Kit for reduction of blood components in a blood-related medium (12), wherein it comprises:
   a gel bead container (1) containing gel beads (2) and provided with an outlet tube (3), wherein the gel beads (2) contain at least one covalently bound antigen or antigen derivative having the ability to bind at least one plasma component,
   a drip chamber (4) provided with an inlet tube (5) and an outlet tube (6), wherein the drip chamber (4) in the bottom thereof is provided with a porous net (14) having a porosity which does not allow passage of the gel beads (2),
   a collection container (10) provided with an inlet tube (11), and
   a medium container (13) adapted to contain a blood-related medium (12) and provided with an outlet tube (15),
   wherein the outlet tube (3) of the gel bead container (1) is connectable with the inlet tube (5) of the drip chamber (4) via a sterile connecting device,
   wherein the outlet tube (6) of the drip chamber is connectable with the inlet tube (11) of the collection container (10) via a sterile connecting device, and
   wherein the outlet tube (15) of the medium container (13) is connectable to the inlet tube (5) of the drip chamber (4) via a sterile connecting device.

2. Kit according to claim 1, wherein the inlet tube (5) of the drip chamber (4) is provided with a clamp (7).

3. Kit according to claim 1, wherein the outlet tube (6) of the drip chamber (4) is provided with a clamp (8) and with a roller clamp (9).

4. Kit according to claim 1, wherein the gel bead container (1), the collection container (10), and the medium container (13) are plastic bags.

5. Kit according to claim 1, wherein each tube is made of plastic and has the same inner diameter.

6. Kit according to claim 1, wherein the gel bead container (1) is a sterilized plastic bag containing a suspension of gel beads (2) in a liquid buffer.

7. Kit according to claim 1, wherein the drip chamber (4) is present in an outer plastic bag and is sterilized.

8. Kit according to claim 1, wherein the medium container (13) contains the blood-related medium.

9. Kit according to claim 8, wherein the blood-related medium is selected from the group consisting of human whole blood, blood plasma, and thrombocytes.

10. Kit according to claim 1, wherein the gel beads (2) contain at least one covalently bound antigen or antigen derivative which selectively bind an antigen specific protein or antibody.

11. Kit according to claim 1, wherein the antigen or antigen derivative contains a protein, a peptide, a carbohydrate, or a carbohydrate derivative.

12. Kit according to claim 11, wherein the carbohydrate derivative contains at least one blood group determinant.

13. Kit according to claim 12, wherein at least one of blood group determinants is a blood group A determinant and/or a blood group B determinant.

14. Kit according to claim 11, wherein the carbohydrate derivative contains at least one of a disaccharide, tri-saccharide, tetra-saccharide and/or a higher oligosaccharide.

15. Kit according to claim 1, wherein the gel beads (2) contain cross-linked agarose, a plastic, polyhydroxymethacrylate or polyhydroxyethylacrylate.

16. Method for the reduction of blood components in a blood-related medium (12) containing a suspension of gel beads (2) by use of the kit according to claim 1, wherein it comprises the steps of:
   a) connecting the outlet tube (3) of the gel bead container (1) with the inlet tube (5) of the drip chamber (4), wherein a clamp (7) of the inlet tube (5) of the drip chamber (4) is closed,
   b) connecting the outlet tube (6) of the drip chamber (4) with the inlet tube (11) of the collection container (10),
   c) agitating the content of the gel bead container (1) containing gel beads (2) to obtain a suspension of gel beads (2),
   d) opening the clamp (7) of the inlet tube (5) of the drip chamber (4),
   e) transfer of the suspension of gel beads (2) to the drip chamber (4), wherein a clamp (8) and a roller clamp (9) of the outlet tube (6) of the drip chamber (4) are closed,
   f) disconnecting the outlet tube (3) of the gel bead container (1) from the inlet tube (5) of the drip chamber (4),
   g) connecting the outlet tube (15) of the medium container (13) containing the blood-related medium (12) with the inlet tube (5) of the drip chamber (4),
   h) opening the clamp (8) of the outlet tube (6) of the drip chamber (4) allowing transfer of the blood-related medium (12) from the medium container (13) to the drip chamber (4) and gradually opening the roller clamp (9) of the outlet tube (6) of the drip chamber (4) until a predetermined flow rate of the blood-related medium (12) is obtained, wherein the level of the blood-related medium (12) in the drip chamber (4) is kept above the level of the gel beads (2),
   i) collecting the blood-related medium (12), which has passed the gel beads (2) in the drip chamber (4), in the collection container (10), wherein the gel beads (2) are prevented from reaching the collection container (10) due to the presence of the porous net (14) provided in the bottom of the drip chamber (4), and
   j) stopping the procedure when the blood-related medium (12) has passed from the medium container (13) to the collection chamber (10) via the drip chamber (4), or, alternatively, closing at least one of the clamp (7) and the clamp (8), replacing the medium container (13) with a new medium container (13) containing a new blood-related medium (12), and repeating steps h)-j).

17. Method according to claim 16, wherein the flow rate of the blood-related medium (12) is measured by counting the number of droplets dripping into the drip chamber (4) for a given time period.

18. Method according to claim 16, wherein the gel beads (2) present in the drip chamber (4) is washed with neutral buffer, followed by washing with acidic glycine buffer, with a view to eluting the component from the blood-related medium (12) bound to the gel beads (2), and collecting the eluted component.

19. Method according to claim 16, wherein the blood-related medium (12) is human whole blood, blood plasma, thrombocytes, or human blood plasma.

20. Method according to claim 16, wherein the suspension of gel beads (2) in the gel bead container (1) instead is transferred to the medium container (13), wherein the suspension of gel beads (2) is mixed with the blood-related medium (12) therein, and wherein the mix of gel beads (2) and blood-related medium (12) then is transferred to the drip chamber (4).

\* \* \* \* \*